United States Patent
Bailey

(10) Patent No.: US 7,600,411 B2
(45) Date of Patent: Oct. 13, 2009

(54) SURFACE FRICTION TESTING APPARATUS

(75) Inventor: Malcolm Bailey, Radlett (GB)

(73) Assignee: Slipalert LLP, Hertfordshire (GB)

( * ) Notice: Subject to any disclaimer, the term of this patent is extended or adjusted under 35 U.S.C. 154(b) by 1 day.

(21) Appl. No.: 10/561,104

(22) PCT Filed: Jun. 7, 2004

(86) PCT No.: PCT/GB2004/002389

§ 371 (c)(1), (2), (4) Date: Aug. 17, 2006

(87) PCT Pub. No.: WO2004/113879

PCT Pub. Date: Dec. 29, 2004

(65) Prior Publication Data

US 2006/0277973 A1    Dec. 14, 2006

(30) Foreign Application Priority Data

Jun. 17, 2003 (GB) ................... 0313970.6

(51) Int. Cl.
*G01N 19/02* (2006.01)
(52) U.S. Cl. .................................................. 73/9
(58) Field of Classification Search ................ 73/9
See application file for complete search history.

(56) References Cited

U.S. PATENT DOCUMENTS

| | | | | |
|---|---|---|---|---|
| 2,018,688 A | * | 10/1935 | Tilden | 73/9 |
| 2,225,140 A | * | 12/1940 | Walker | 73/9 |
| 2,299,895 A | * | 10/1942 | Harrall et. al. | 73/9 |
| 3,083,029 A | * | 3/1963 | Russell | 280/659 |
| 3,301,039 A | * | 1/1967 | Kummer | 73/9 |
| 3,376,730 A | * | 4/1968 | Webb | 73/9 |
| 3,828,605 A | | 8/1974 | Fazekas | |
| 3,893,330 A | | 7/1975 | Shute et al. | |
| 3,975,940 A | * | 8/1976 | Brungraber | 73/9 |
| 4,003,241 A | * | 1/1977 | Thomas | 73/9 |
| 4,187,714 A | * | 2/1980 | Cox et al. | 73/9 |
| 4,315,426 A | * | 2/1982 | Brandon | 73/9 |
| 4,594,878 A | * | 6/1986 | Abe et al. | 73/9 |

(Continued)

FOREIGN PATENT DOCUMENTS

AU    70212 74 A    12/1975

(Continued)

OTHER PUBLICATIONS

Hallas et al., "Evaluation of the Kirchberg Rolling Slider and SlipAlert Slip Resistance Meters", 2006, pp. 1-35.*

(Continued)

*Primary Examiner*—David A. Rogers
(74) *Attorney, Agent, or Firm*—Christie, Parker & Hale, LLP

(57) ABSTRACT

Surface testing friction apparatus comprises a trolley and an inclined ramp. The trolley and ramp are arranged such that a slider on the trolley comes into contact with the surface during a test run over a surface, the friction coefficient of which is to be determined, the mass of the trolley length and a height of the ramp are selected such that for a slider of given properties, materials and dimensions the critical film thickness for a wet surface is approximately 2 μm.

16 Claims, 3 Drawing Sheets

U.S. PATENT DOCUMENTS

| | | | | |
|---|---|---|---|---|
| 4,759,209 | A | * | 7/1988 | Brungraber ..................... 73/9 |
| 4,813,266 | A | | 3/1989 | Nash |
| 5,107,448 | A | * | 4/1992 | Nash ........................ 702/141 |
| 5,245,856 | A | * | 9/1993 | Pazzaglia et al. ................ 73/9 |
| 5,259,236 | A | * | 11/1993 | English ........................ 73/9 |
| 5,576,478 | A | * | 11/1996 | Brungraber ..................... 73/9 |
| 5,722,675 | A | * | 3/1998 | Yang ........................ 280/244 |
| 6,145,382 | A | * | 11/2000 | Nagasawa et al. ............ 73/664 |
| 6,554,298 | B1 | * | 4/2003 | Bidwell ................... 280/47.11 |
| 6,612,151 | B2 | * | 9/2003 | Haines .......................... 73/9 |
| 6,860,139 | B2 | * | 3/2005 | Pelz ............................. 73/9 |
| 7,117,716 | B2 | * | 10/2006 | Neubert et al. .................. 73/9 |
| 2001/0047679 | A1 | * | 12/2001 | Haines .......................... 73/9 |

FOREIGN PATENT DOCUMENTS

| | | | |
|---|---|---|---|
| DE | 42 01 124 | A | 7/1993 |
| GB | 1 090 828 | A | 11/1967 |
| GB | 1 542 546 | | 3/1979 |
| JP | 54153088 | A * | 12/1979 |
| JP | 03018741 | A * | 1/1991 |
| JP | 2001 296239 | | 10/2001 |
| JP | 2002-310890 | | 10/2002 |
| SU | 815604 | A | 3/1981 |
| SU | 1396001 | A | 5/1998 |
| WO | WO 98/35218 | A | 8/1998 |
| WO | WO 01/61315 | A1 | 8/2001 |

OTHER PUBLICATIONS

Kirchberg et al., "In situ measurement of sliding friction of floors: study for the optimization of check parameters", 1997.*

Official Translation of Kirchberg et al., "In situ measurement of sliding friction of floors: study for the optimization of check parameters", 1997.*

Patent Abstracts of Japan, Publication No. 2002310890; Publication Date: Oct. 23, 2002; in the name of Noda.

Search Report for corresponding British Application No. GB 0313970.6 dated Oct. 31, 2003.

Patent Abstracts of Japan for Publication No. 01276044A; Date of Publication Nov. 6, 1989; in the name of Yamaguchi et al.

Patent Abstracts of Japan for PublicationNo. 2001296239; Date of Publication Oct. 26, 2001; in the name of Riku.

UNKNOWN, "The Measurement of the Slip Resistance of Floor Surface The Tortus and the Pendulum", Construction & Building Materials, Sep. 1988, vol. 2 No. 3, pp. 163-171.

International Search Report, Dated Oct. 08, 2004, Corresponding to PCT/GB2004/002389.

* cited by examiner

Typical curve of sliding length - vs - μ(coeficient of friction)

SURFACE FRICTION TESTING APPARATUS

CROSS-REFERENCE TO RELATED APPLICATION

This application is a National Phase Patent Application of International Application Number PCT/GB2004/002389, filed on Jun. 7, 2004, which claims priority of British Patent Application Number 0313970.6, filed on Jun. 17, 2003.

The present invention relates to surface friction testing apparatus for determining the coefficient of friction of a surface and particularly, but not exclusively, to a surface friction testing apparatus for testing coefficient of friction of a pedestrian walkway. The apparatus though can equally be used for measuring the coefficient of friction of a roadway for vehicles.

With liability issues becoming more prevalent it is important that the coefficient of friction of a pedestrian surface can be determined, with a relatively high degree of accuracy, when dry, and more importantly when wet.

Prior art friction testing devices have comprised powered trolleys, or trolleys arranged to be pulled across a surface, which trolleys have resistance material in contact with the surface over which they travel. Such prior art trolleys may give satisfactory results in dry conditions but in wet conditions they fail to simulate the characteristics of the lubricating film under a pedestrians foot as it slips.

A trolley has been designed to compare but not measure the coefficient of friction of artificial sports surfaces where the mass of the trolley is sufficient to reproduce the actual force between the heel and the ground, requiring a trolley weighing some 30 to 40 kilograms. This precludes the device from being portable, thus it finds limited application because it is normally necessary to transport the device to the surface to be tested, for example to a pedestrian surface where a person is known to have slipped.

One piece of equipment that is portable is a device used by the British Transport and Road Research Laboratory, which device was primarily developed for testing the friction coefficient of roads. This gives accurate results for both wet and dry conditions and is now the British health and safety standard. The device comprises a tripod arrangement supporting a pendulum arranged to be released from a set height, the pendulum terminating in a pad of friction material arranged to contact the surface to be tested at the bottom of the pendulum swing over a specific length of contact (ie 125 mm). The height to which the pendulum rises is representative of the friction coefficient of the surface, the greater the height the lower the coefficient of friction. Although this device is relatively portable, it requires both a considerable amount of time and experience to set it up, requiring that the tripod be perfectly level and correctly spaced from the ground. It also requires that the ground. The coefficient of friction given by this machine is often referred to as the slip resistance.

The object of the present invention is to provide portable surface friction testing apparatus which is easy to transport, set up and operate.

According to the present invention there is provided portable surface friction testing apparatus for determining the coefficient of friction of a surface, the apparatus consisting of a body, the underside of which is fitted with at least one slider to induce friction between the body and the test surface as the body moves across the test surface, and means of propelling that body to a predetermined initial velocity at the commencement of a test run over which test run the coefficient of friction of the surface is determined by reference to the distance required to cause the at least one slider to bring the body to a standstill.

Note that under deceleration the force on the slider will depend on the precise position of the centre of gravity of the trolley (both vertically and horizontally) and the degree of declaration.

The present invention provides a relatively simple device whereby the coefficient of friction can be determined from the distance travelled during the test run of the body. The body decelerating during the test run produces slippage characteristics similar to those experienced by a pedestrian foot as it commences a slip.

Preferably, the body is in the form of a trolley comprising wheels in contact with the ground for providing, together with the at least one slider, directional stability to the trolley, the wheels and at least one slider all positioned such that the force between the at least one slider and the surface can be determined and remains constant under any particular value of uniform deceleration.

Advantageously, the trolley is arranged to have two wheels in contact with the ground during the test run, with a single slider forming the third point of contact with the ground. Having three points of contact ensures mass on each is uniform during the test run even if the test run is uneven.

Advantageously, the means for propelling the trolley comprises a ramp of known incline and length. The ramp may be collapsible to assist in transport and preferably comprises a stop at its upper end against which the trolley is held prior to release. The ramp and trolley are pre-calibrated such that velocity of the trolley is known at the point from which it commences its test run, when the slider comes into contact with the surface under test.

The trolley preferably comprises at least one addition wheel wherein the ramp and trolley are arranged such that the at least one addition wheel supports the trolley on the ramp during the period in which the trolley accelerates down the ramp, but wherein the mass on the at least one wheel is transferred to the slider at the commencement of the test run. This ensures that the acceleration of the trolley is not affected by any change in coefficient of friction that may otherwise exist between the slider and the ramp if these were in contact.

Advantageously, the trolley is propelled during the test run only by the initial kinetic energy of the trolley until the trolley comes to rest, the distance travelled during the test run being indicative of the coefficient of friction of the surface over which the trolley has travelled. This is particularly advantageous for the result will correspond to an average for the area over which the trolley has travelled. Thus, the apparatus in accordance with the invention provides more reliable results on surfaces where the coefficient of friction may not be uniform over the surface.

Preferably, the coefficient of friction of the slider, the mass acting on the slider, the speed at commencment of the test run and dimensions of the slider in contact with the surface under test are selected such that, when the test surface is wet, the hydrodynamic critical film thickness developed is in the range of 1 to 3 μm. More specifically, the hydrodynamic critical film thickness developed is preferably in the range of 1.5 to 2.5 μm, and even more specifically in the range of 1.9 to 2.1 μm.

Advantageously, the apparatus comprises means for determining the distance travelled by the trolley and for automatically calculating from this the coefficient of friction for the test run.

Preferably, the apparatus comprises a look up table or graph for determining the coefficient of friction from the distance travelled, and the trolley determines the distance travelled and displays the corresponding coefficient of friction.

It has been found particularly advantageous if a trolley has two wheels in contact with the ground during the test run. Two wheels preferably being on a common axis and locked together, for this further improves directional stability.

Preferably, the mass of the trolley is less than 6 kg thereby providing a portable device.

The present invention provides for portable friction testing apparatus employing a relatively light weight trolley. In dry conditions with simple 'couloumb' friction, reducing the mass of trolley would have little or no effect on the results since the value of µ is independent of R in the standard friction equation $$\mu = F/R$$

where F is the frictional force acting along the surface and R is the vertical reaction force between the sliding body and surface, µ being the coefficient of friction. However, when the surface is wet and thus a lubricant is involved, as in wet pedestrian slipping, which is an area of particular interest, µ is no longer independent of R.

The invention, unlike all previous devices for measuring wet pedestrian slipping, recognises that the key factor in scaling from the full sized non-portable device down to a light portable device is that the characteristics of the hydrodynamic lubricating film of the full sized device should be accurately reproduced in the small sized device. If, and only if, these characteristics are reproduced will the model give identical results to that of the full sized version, in this case a pedestrian as he slips over the range of surfaces likely to be tested.

In order to achieve this, the characteristics of the lubricating film can be produced only if what is known as the 'critical film thickness' is the same in both the model and the fill sized event, ie a slipping pedestrian. This 'critical film thickness' is a standard concept in lubrication but has never until now been applied to the design of pedestrian slip test device.

The critical film thickness, $h_{cr}$, is given by the following equation $$h_{cr} = \sqrt{\frac{6\eta u l K \varepsilon K \rho}{Pav}}$$

where:
η=viscosity of the liquid (in the case of water $1\times10^3$ N/m²)
u=relative velocity of the two surfaces
l=length of the film formed
b=breadth of the film
$K\varepsilon$=a factor dependant on the b/l ratio which affects the load carrying capacity of the film due to side leakage
$K_\rho$=a factor which depends on the geometry of the film wedge but which is taken as 0.025 in the case of pedestrian slipping
Pav=the average pressure of the film=F/bl
F=the total vertical force on the film (eg the vertical force on the slider)

The way that the lubricating film works is to provide an uplift to the sliding body thus reducing its contact with the underlying surface and thus the friction between the two. In essence, if the 'model' has a critical film thickness which is much lower than that for a slipping pedestrian it will only experience an uplift on very smooth surfaces and thus give a low value for µ for those surfaces. While it will indicate that these are dangerous for a pedestrian, it will suggest that a range of not quite so smooth surfaces are quite safe even through they in practice are such as to a cause a pedestrian to slip over. Virtually all known slip test devices suffer from this.

In contrast to the above, if a model has too high a value of critical film thickness, it will experience an uplift over far too wide a range of surfaces, those at the rougher end may well in practice be relatively safe for pedestrians. It is therefore important that the critical film thickness of the model or test machine matches reasonably closely that of a slipping pedestrian.

One embodiment of the present invention will now be described, by way of example only, with reference to the accompanying figures, of which:

Figure 1:
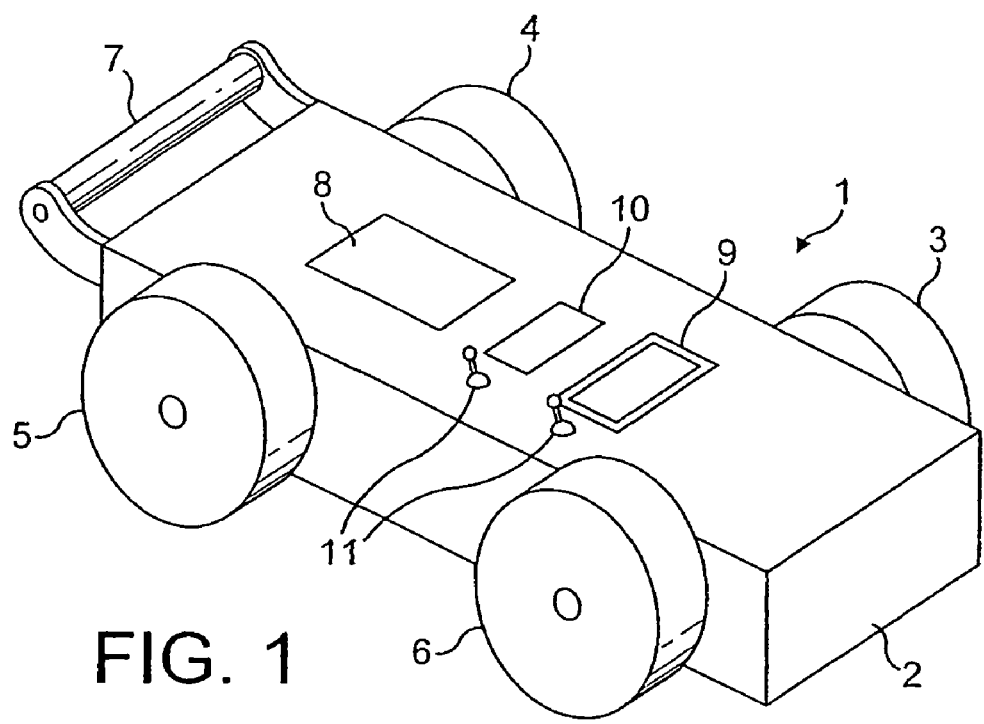
FIG. 1 is a perspective view of a trolley in accordance with the present invention.

Referring to FIG. 1, a 5 kg trolley indicated generally as 1 comprises a main body 2, wheels 3 to 6, a handle 7, electronics pack 8, a display 9 showing the distance travelled an ON/OFF switch and indicator lights 11, one of which lights up when the trolley is correctly at the point of return at the top of the ramp.

Figure 2:
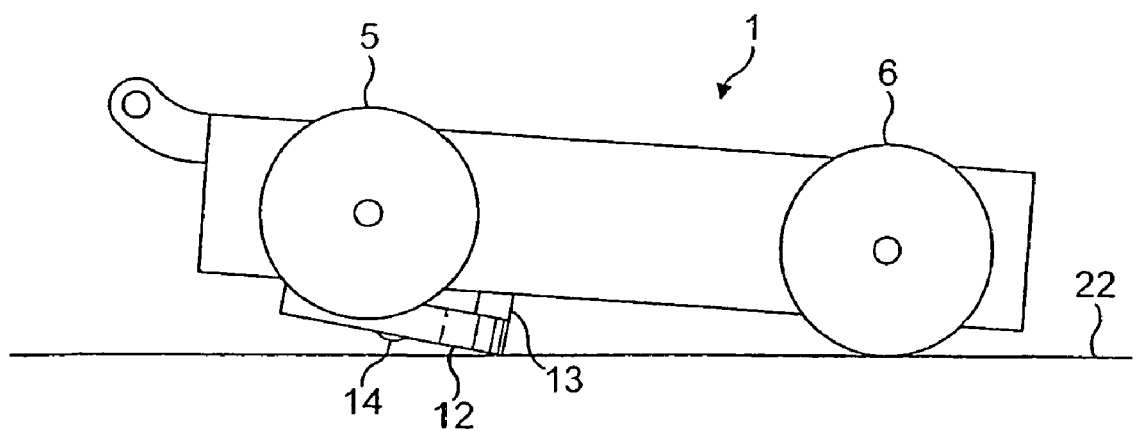
FIG. 2 is a side elevation of a trolley of FIG. 1.

As shown in FIG. 2, the trolley additionally comprises a slider 12 spaced from the trolley by spacer 13 and held in place by screw-fixing 14. The slider 12 is composed of Four S rubber disclosed in British standard BS 7976, which is herein incorporated by way of reference.

The apparatus in accordance with the invention additionally comprises a ramp, indicated generally as 15, the ramp 15 comprising an inclined portion 16 having a length L of 900 mm and a leg 17 arranged such that the front face of stop 18 intersects the incline at a height 'H' of 200 mm. The ramp 15 is hinged by hinges 19 and 20 such that the incline 16 may be folded in half and the leg 17 folded flush with the incline to assist transportation.

The front wheels 3 and 6 of the trolley 1 are linked together on a common axle (not shown) such as to maintain directional stability of the trolley. A sensor on the axle (not shown) additionally provides information to the electronic module 8 relating to the distance travelled.

Figure 3:
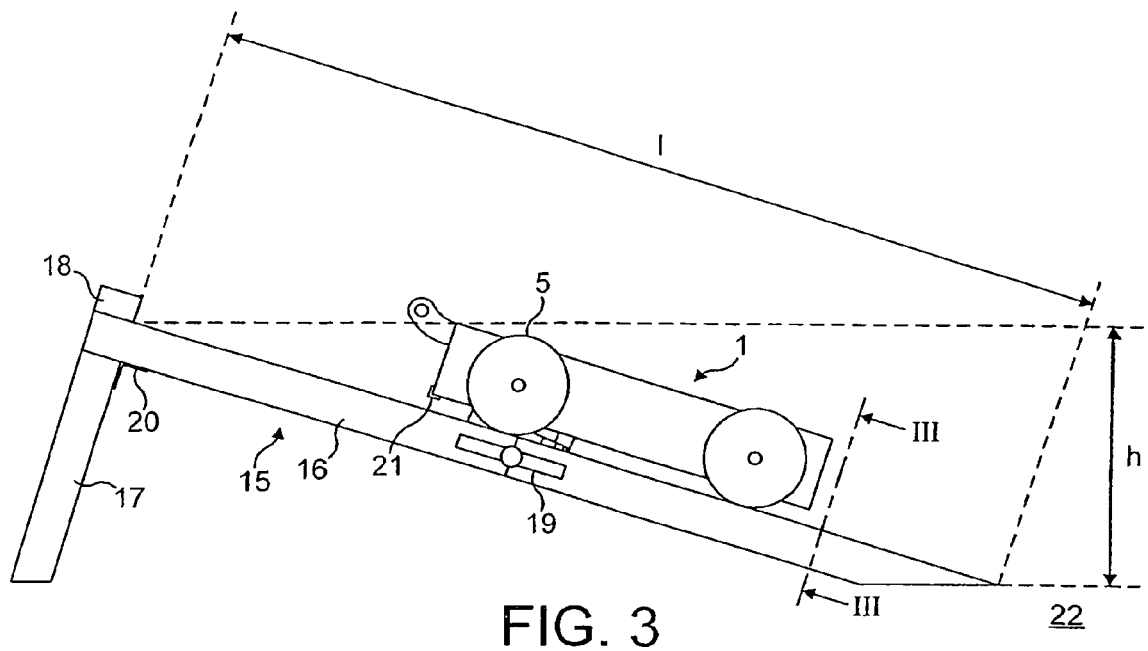
FIG. 3 is a side elevation of a trolley of FIGS. 1 and 2 shown positioned on a ramp in accordance with the present invention.
Figure 4:
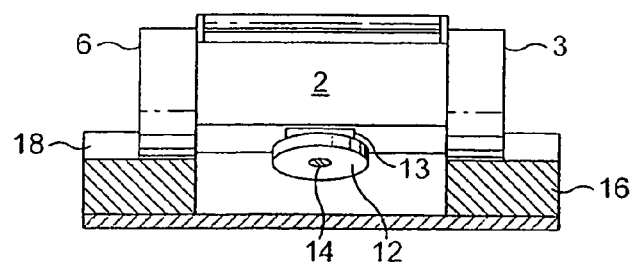
FIG. 4 is a cross section through the III-III of FIG. 3.

In operation, the ramp is erected as shown in FIG. 3 and the trolley pulled to the top of the ramp such that the rear face of the trolley is against the stop 18. At this point a sensor 21 detects that the trolley is at the top of the ramp and transmits this to the electronics module 8 and one of the indicator lamps 11.

The trolley is released from its starting point, and free wheels on wheels 3 to 6 to the bottom of the ramp. During the decent of the ramp, the slider 12 is supported by the rear wheels 5 running on the rails of the incline 16. The mass of the trolley is 5 kg and the trolley reaches a velocity of 2 m/sec. This commences the test run as the slider comes into contact with ground.

During the test run the trolley travels until its kinetic energy is depleted, with the primary deceleration force resulting from the slider 14 being in contact with the surface 22 for which the coefficient of friction is to be determined. The electronic module indicates the total distance travelled from the top of the ramp to when the trolley comes to rest; the corresponding coefficient of friction for the test surface is identified from the graph shown in FIG. 5.

Figure 5:
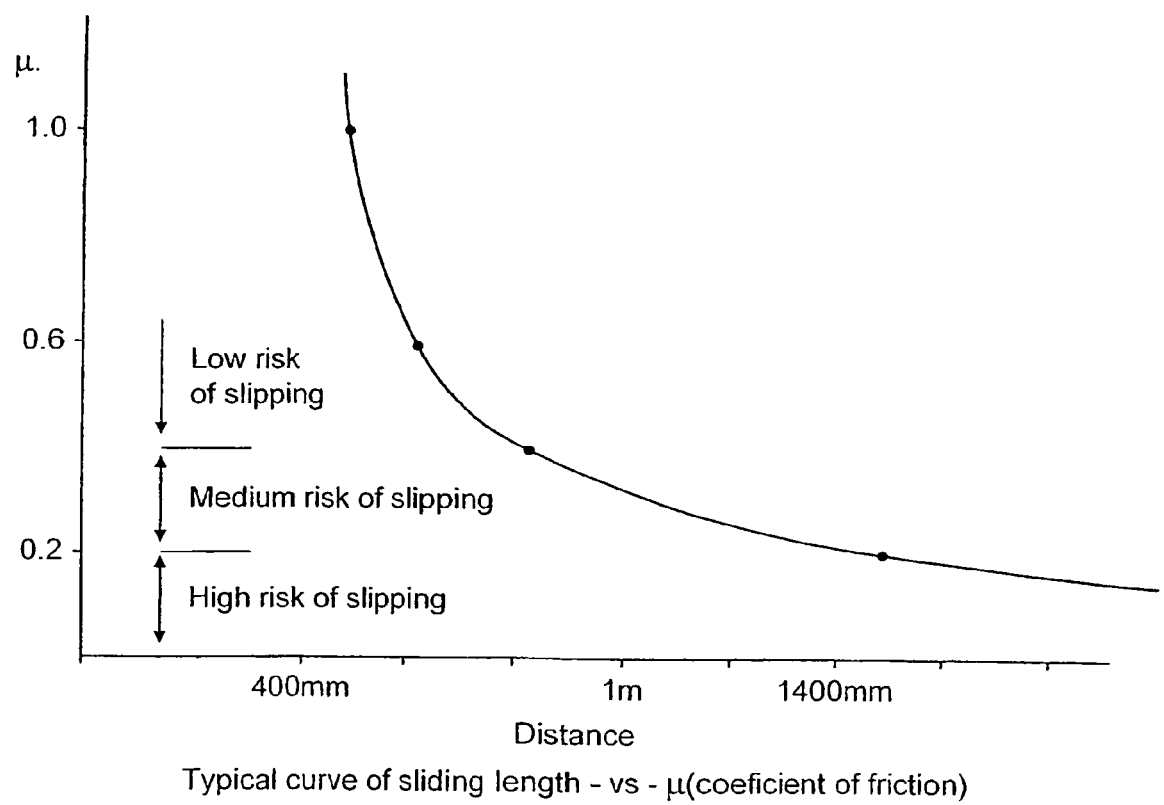
FIG. 5 is graph of µ versus the distance of travel of the trolley in accordance with invention prepared based on theoretical dynamics and checked using the test results using the British standard pendulum device described in British standard BS 7976.

FIG. 5 is based on the formula derived from dynamic theory such that $$s = u^2 \tfrac{1}{2} \mu (a - b\mu) g$$

where s=distance to come to rest
u=initial velocity
l=horizontal distance from front axle to slider contact position
$\mu$=coefficient of friction
a=horizontal distance from front axle to centre of gravity of trolley
b=height of centre of gravity above test surface
g=acceleration due to gravity The mass of the slider, initially velocity, surface area and friction properties of the slider 12 are selected such that the average critical film thickness on a wet surface is in the range of 1.9 to 2.1 µm.

In a practical example, the critical film thickness using N, m, sec units $$h_{cr} = \sqrt{\frac{6\eta u l^2 b K_\varepsilon K_p}{F}}$$

$$= \sqrt{\frac{6 \times (1 \times 10^{-3}) \times 1.0 \times (4.5 \times 10^{-3})^2 \times (40 \times 10^{-3}) \times 0.95 \times 0.025}{3 \times 9.81}}$$

$$= 2 \times 10^{-6} m$$

One embodiment of the invention has been described above, however various alternative embodiments and modifications will be apparent to one skilled in the art, which are within the scope of the appended claims.

The invention claimed is:

1. A portable surface friction testing apparatus for determining a coefficient of friction of a test surface during a test run, the apparatus comprising a trolley having a mass and comprising a first plurality of wheels for contacting the test surface throughout the test run, at least one additional wheel, and an underside fitted with at least one slider to induce friction between the body and the test surface as the body moves across the test surface wherein the first plurality of wheels and the at least one slider provide directional stability to the trolley, and are positioned such that a force between the at least one slider and the test surface can be determined and remains constant under any particular value of uniform deceleration; and a ramp of known incline and length adapted to propel the body to an initial velocity of the test run wherein the ramp and the trolley are arranged such that the at least one additional wheel bears a portion of the mass of the trolley on the ramp during a period in which the trolley accelerates down the ramp, but wherein the portion of the mass of the trolley borne by the at least one additional wheel is transferred to the at least one slider at commencement of the test run.

2. The apparatus as claimed in claim 1, wherein a single slider forms a third point of contact with the test surface.

3. The apparatus as claimed in claim 1 wherein the trolley comprises two wheels arranged to be in contact with the test surface during the test run, the two wheels being on a common axis and locked together to improve direction stability.

4. The apparatus as claimed in claim 1, wherein over the test run the coefficient of friction of the test surface is determined by reference to a distance required by the at least one slider to bring the body to a standstill, wherein the dimensions of the at least one slider, a force on the at least one slider and the initial velocity of the test run are selected such that when the test surface is wet a hydro-dynamic critical film thickness is developed in the range from about 1 to 3 µm.

5. A portable surface friction testing apparatus for determining a coefficient of friction of a test surface, the apparatus comprising a body including an underside fitted with at least one slider to induce friction between the body and the test surface as the body moves across the test surface, and means of propelling the body to an initial velocity of a test run over which the coefficient of friction of the test surface is determined by reference to a distance required by the at least one slider to bring the body to a standstill, wherein:
  the body is a trolley having a mass and comprising a first plurality of wheels in contact with the test surface for providing, together with the at least one slider, directional stability to the trolley, the first plurality of wheels and the at least one slider positioned such that a force between the at least one slider and the test surface can be determined and remains constant under any particular value of uniform deceleration;
  the trolley has two of the first plurality of wheels in contact with the test surface during the test run, with a single slider forming a third point of contact with the test surface;
  the means for propelling the trolley comprises a ramp of known incline and length; and
  the trolley comprises at least one additional wheel and the ramp and trolley are arranged such that the at least one additional wheel bears a portion of the mass of the trolley on the ramp during a period in which the trolley accelerates down the ramp, but wherein the portion of the mass of the trolley born by the at least one additional wheel is transferred to the at least one slider at commencement of the test run.

6. The apparatus as claimed in claim 5, wherein the body is propelled during the test run only by the initial kinetic energy of the body until the body comes to rest, a distance traveled during the test run being indicative of the coefficient of friction of the surface over which the body has traveled.

7. The apparatus as claimed in claim 5, wherein the at least one slider is a plastic or rubber material.

8. The apparatus as claimed in claim 5, wherein the mass of the trolley body is less than 6 kg.

9. The apparatus as claimed in claim 5, wherein the first plurality of wheels comprises two wheels on a common axis and locked together to improve direction stability.

10. The apparatus as claimed in claim 5 wherein the dimensions of the at least one slider, a force on the slider and the initial velocity are selected such that when the test surface is wet a hydro-dynamic critical film thickness is developed in the range from about 1 to 3 μm.

11. The apparatus as claimed in claim 10, wherein the hydro-dynamic critical film thickness developed is in the range from about 1.5 to 2.5 μm.

12. The apparatus as claimed in claim 11, wherein the hydro-dynamic critical film thickness developed is in the range from about 1.9 to 2.1 μm.

13. The apparatus as claimed in claim 5, wherein the apparatus comprises means for determining the distance traveled by the body.

14. The apparatus as claimed in claim 13, wherein the distance traveled is used to calculate the coefficient of friction for the test surface.

15. The apparatus as claimed in claim 14, further comprising a look-up table or graph for determining the coefficient of friction corresponding to the distance traveled by the body.

16. The apparatus as claimed in claim 14, wherein the body determines and displays the coefficient of friction.

* * * * *